United States Patent [19]

Najer et al.

[11] 4,265,911
[45] May 5, 1981

[54] PROPIONAMIDOXIME DERIVATIVES

[75] Inventors: Henry Najer, Paris; Daniel Obitz, Orsay, both of France

[73] Assignee: Synthelabo, Paris, France

[21] Appl. No.: 82,656

[22] Filed: Oct. 9, 1979

[51] Int. Cl.³ .................. A61K 31/155; C07C 123/00
[52] U.S. Cl. .................. 424/326; 564/258
[58] Field of Search .............. 260/566 A, 564 G; 424/326, 327

[56] References Cited

U.S. PATENT DOCUMENTS 3,394,181  7/1968  Bell .................................. 260/566 A

OTHER PUBLICATIONS

Areschka, Alex et al., *Eur. J. Med. Che.-Chim. Ther.*, (1975), vol. 10(5) 463-469.

*Primary Examiner*—Natalie Trousof
*Assistant Examiner*—L. Hendriksen
*Attorney, Agent, or Firm*—Wegner & Bretschneider

[57] ABSTRACT

Propionamidoxime derivatives which are compounds of formula (I)

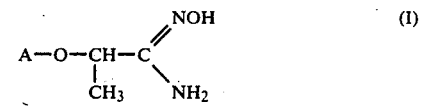

in which A is a tetrahydronaphthyl or dihydronaphthyl radical and their pharmaceutically acceptable salts are valuable for treatment of the central nervous system and depression.

The above compounds are prepared by reacting the nitrile (II)

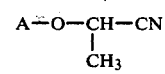

with hydroxylamine hydrochloride.

6 Claims, No Drawings

PROPIONAMIDOXIME DERIVATIVES

DESCRIPTION

The present invention relates to propionamidoxime derivatives, their preparation and pharmaceutical compositions containing them.

The propionamidoxime derivatives of the invention are compounds of formula (I)

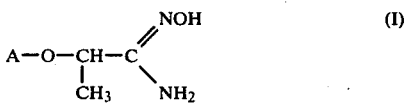

in which A is a tetrahydronaphthyl or dihydronaphthyl radical and their pharmaceutically acceptable acid addition salts.

These compounds possess an asymmetric carbon. The invention therefore includes the racemates and the optically active isomers of the compounds (I).

According to the invention, the propionamidoxime derivatives can be prepared by a process which comprises reacting the nitrile

with hydroxylamine hydrochloride, normally under substantially anhydrous reaction conditions, effective to prevent hydrolysis of the nitrile to the acid as a predominant reaction, preferably at a temperature of from 50° to 120° C. and preferably in an inert organic solvent. A free base thereby obtained can be converted to its acid addition salt.

The nitriles (II), which are new intermediates, can be obtained from the corresponding naphthols by conventional reactions, namely esterification of the naphthol, formation of the amide and then dehydration of the amide, or direct nitrilation of the naphthol with a 2-halopropionitrile.

The process according to the invention can be carried out in a solvent, e.g. ethanol, in the presence of sodium ethylate (sodium ethoxide), at e.g. the reflux temperature of the solvent.

The following Examples illustrate the invention. The analyses and the IR and NMR spectra confirmed the structure of the compounds.

EXAMPLE 1:

2-(5,6,7,8-Tetrahydronaphthyl-1-oxy)-propionamidoxime and its hydrochloride.

1. Methyl 2-(5,6,7,8-tetrahydronaphthyl-1-oxy)-propionate 39.87 g (0.270 mol) of 5,6,7,8-tetrahydro-α-naphthol and 37.3 g (0.270 mol) of potassium carbonate in 100 cm³ of methyl ethyl ketone are heated under reflux for half an hour.

The mixture is cooled and 50.1 g (0.3 mol) of methyl 2-bromopropionate are added. The mixture is heated under reflux for 20 hours. It is cooled and filtered.

The filtrate is evaporated to dryness. The product obtained is taken up in ether and the mixture is washed with 5% strength sodium hydroxide solution and with water and then dried over magnesium sulphate. Boiling point (0.05 mm Hg)=125° C.

2. 2-(5,6,7,8-Tetrahydronaphthyl-1-oxy)-propionamide 54.93 g (0.235 mol) of the above ester in 220 cm³ of ethanol and 220 cm³ of concentrated ammonia solution are stirred at ambient temperature.

After one hour, the product starts to precipitate. 200 cm³ of water are added. The mixture is stirred for 2 hours. 200 cm³ of ice-cooled water are added and the solid is filtered off, washed with water and dried. The described product is obtained. Melting point=16-1°-163° C.

3. 2-(5,6,7,8-Tetrahydronaphthyl-1-oxy)-propionitrile 45.2 g (0.206 mol) of the above amide and 150 g of phosphorus pentoxide in 1 liter of dry toluene are heated under reflux for 3 hours in a 2 liter reactor equipped with a stirrer. The toluene layer is decanted, the gummy part is washed with chloroform, the chloroform extracts are combined with the toluene layer, the whole is washed with water until the washings are neutral, dried over magnesium sulphate and filtered, the solvent is evaporated off from the filtrate and the residue is rectified. Boiling point (0.15 mm Hg)=133°-134° C.

4. 2-(5,6,7,8-Tetrahydronaphthyl-1-oxy)-propionamidoxime 26.99 g (0.134 mol) of the above nitrile in 200 cm³ of anhydrous ethanol are heated to the reflux temperature. 16.75 g (0.241 mol) of hydroxylamine hydrochloride, dissolved in 300 cm³ of dry ethanol, are added.

A solution of sodium ethylate, prepared beforehand by dissolving 5.54 g (0.241 mol) of sodium in about 150 cm³ of dry ethanol, is added dropwise. Heating under reflux is continued for 5 hours, the mixture is filtered, the solvent is evaporated off from the filtrate, the residue is taken up in chloroform, the chloroform solution is washed with water and dried over magnesium sulphate, the solvent is evaporated off and the oily residue is crystallised from petroleum ether. After recrystallisation from cyclohexane, the product melts at 102°-103° C.

5. Hydrochloride 23 g (0.0983 mol) of 2-(5,6,7,8-tetrahydronaphthyl-1-oxy)-propionamidoxime are dissolved in a small amount of ethanol. A solution of hydrogen chloride in ether is added and the mixture is evaporated to dryness. The resulting solid is triturated in ether and washed with ether and then washed once with a small amount of acetone. It is recrystallised from an ethanol/ether mixture. The hydrochloride is obtained. Melting point=18-7°-188.5° C.

EXAMPLE 2:

2-(5,8-Dihydronaphthyl-1-oxy)-propionamidoxime and its hydrochloride.

1. 5,8-Dihydro-1-naphthol 108 g (0.75 mol) of α-naphthol are placed in a 4 liter reactor. The round-bottomed flask is cooled in a bath of solid carbon dioxide and alcohol, and about 1 liter of liquid ammonia is introduced, whilst stirring vigorously. When the naphthol has almost dissolved, 20.9 g of lithium wire are added in small pieces and the mixture is then stirred for ½ hour. 170 ml of ethyl alcohol are then poured in dropwise. The round-bottomed flask is then left to warm up and nitrogen is bubbled into the mixture in order to drive off the ammonia. The grey pasty residue is taken up in 1 liter of water and the mixture is extracted 3 times with 100 ml of ether. The aqueous phase is cooled and acidified with concentrated HCl until the pH is acid. The brown oil which has appeared is extracted 3 times with ether and the ether fraction is washed 3 times with water before being dried over magnesium sulphate. After filtration and evaporation to dryness, the solid is taken up in ether and the mixture is dried over $M_gSO_4$ in the presence of charcoal. The mixture is filtered and the filtrate is evaporated to dryness. A yellow solid is obtained. After recrystallisation, a white solid is finally obtained. Melting point = 73°–74.5° C.

2. 2(5,8-Dihydronaphthyl-1-oxy)-propionitrile 3.85 g (0.08 mol) of sodium hydride are placed in a 250 ml Erlenmeyer flask, washed 4 times with petroleum ether and then covered with 100 ml of DMF. A solution of 11.7 g (0.08 mol) of 5,8-dihydro-1-naphthol in 25 ml of DMF is poured dropwise into the mixture. A small amount of potassium iodide is added to the resulting brown solution, and a solution of 7.3 g (0.08 mol) of 2-chloropropionitrile in 25 ml of DMF is then added dropwise. The mixture is left to react overnight at ambient temperature and then for 6 hours at 90° C. The DMF is evaporated off in vacuo. The residue is taken up between water and ether, a black resin is filtered off and the ether phase is decanted, washed several times with water and dried over magnesium sulphate. After filtration and evaporation to dryness, a pale yellow solid remains. It is recrystallised from hexane. A light beige solid is obtained. Melting point = 60°–61.5° C.

3. 2-(5,8-Dihydronaphthyl-1-oxy)-propionamidoxime 8.95 g (0.0449 mol) of the above nitrile and 3.12 g (0.0449 mol) of hydroxylamine hydrochloride are mixed with 75 cm³ of ethanol, and a solution of sodium ethylate, prepared from 1.03 g of sodium in 40 ml of ethanol, is then added dropwise. The mixture is subsequently heated under reflux for 5 hours. The precipitate of NaCl is filtered off and the filtrate is evaporated to dryness. The residue is taken up in ether, a small amount of benzene and water, the mixture is stirred and the organic phase is decanted. It is washed with water and then dried over magnesium sulphate and charcoal. The mixture is filtered and the filtrate is evaporated to dryness. A spontaneously crystalline white solid is obtained. It is recrystallised twice from cyclohexane containing a small amount of benzene. Melting point = 117°–118° C.

4. Hydrochloride 5 g (0.0215 mol) of the above base are dissolved in about 150 ml of ether and a few ml of ethanol, and a solution of hydrochloride in ether is added dropwise until the pH is acid. A fine white solid precipitates immediately. The crystallisation is allowed to proceed to completion in the cold and this solid is then filtered off, washed with ether and dried.

After recrystallisation, a fine white solid is obtained. Melting point = 172°–173° C. (decomposition).

EXAMPLE 3:

2-(7,8-Dihydronaphthyl-1-oxy)-propionamidoxime and its hydrochloride.

1. 7,8-Dihydro-1-naphthol 57 g of extremely pure dimethylsulphoxide are placed in a 100 ml Erlenmeyer flask with a ground glass joint and its temperature is stabilised at 160°. 19 g (0.1157 mol) of 1,5-dihydroxy-1,2,3,4-tetralin are then added thereto and the reaction mixture is kept at this temperature for 4 hours 30 minutes. The greatest possible amount of DMSO is evaporated off using a vacuum pump and the residue is taken up between 400 ml of ether and 90 ml of water. A black resin is filtered off and the filtrate is separated by decantation. The organic phase is subsequently washed 6 times with water and then dried over magnesium sulphate in the presence of charcoal. The mixture is filtered and the filtrate is evaporated to dryness. A brown oil is obtained. After sublimation of the oil, a solid is obtained which is recrystallised from a mixture of heptane and hexane (50/50). After further sublimation of the reaction mixture on an adiabatic column, the product is recrystallised from hexane and a solid is recovered in the form of fine white needles. Melting point = 67°–68° C.

2. 2-(7,8-Dihydronaphthyl-1-oxy)-propionitrile 4.6 g (0.0958 mol) of a 50% strength dispersion of sodium hydride in oil are placed in a round-bottomed flask with a ground glass joint, washed 4 times with petroleum ether by decantation and then covered with 125 ml of extremely pure DMF. The atmosphere is purged with nitrogen and a solution of 13.7 g (0.0937 mol) of the above naphthol in 30 ml of DMF is introduced dropwise onto this stirred suspension.

A slight warming and the appearance of a uniform evolution of gas are observed. After the addition, the introduction of sodium is left to proceed to completion for a further 1 hour at ambient temperature. A solution of 8.4 g (0.0937 mol) of 2-chloropropionitrile in 30 ml of DMF is subsequently poured in dropwise and the mixture is then stirred for 2 hours and left to stand overnight.

The DMF is evaporated off to dryness, the residue is taken up between water and ether and the ether phase is decanted. The aqueous phase is re-extracted twice with ether and the organic phases are combined and washed several times with water until the washings are neutral. The organic phase is dried over magnesium sulphate in the presence of charcoal, the mixture is filtered and the filtrate is evaporated. A light yellow oil is recovered.

After elution of the product with toluene on a dry alumina column (TSC Woelm), the product is extracted with ether and the mixture is evaporated to dryness. A pale yellow oil is obtained which crystallises to give a white solid. Melting point = 45°–46.5° C.

3. 2-(7,8-Dihydronaphthyl-1-oxy)-propionamidoxime 6.97 g (0.035 mol) of the above nitrile and 2.43 g (0.035 mol) of hydroxylamine hydrochloride are introduced into a 100 ml Erlenmeyer flask with a ground glass joint and 60 ml of ethanol are added thereto. This suspension is stirred magnetically for a few minutes and a solution of sodium ethylate, prepared from 0.8 g (0.035 mol) of sodium in 35 ml of ethanol, is then poured in slowly. The disappearance of the hydrochloride and the concomitant appearance of a fine precipitate of sodium chloride are observed. The mixture is heated to the reflux temperature of the solvent and kept at this temperature for 5 hours. The precipitate is filtered off and washed with alcohol and the filtrate is evaporated to dryness. The resulting viscous oil is taken up in ether and benzene and the mixture is then washed several times with water and dried over magnesium sulphate. After filtration and evaporation of the filtrate, a thick yellow oil remains which is dissolved in hot cyclohexane; in light beige solid crystallises from this solution and is filtered off, washed and dried.

After recrystallisation from cyclohexane and drying in vacuo, the solid melts at 77.5°–78.5° C.

4. Hydrochloride 5.1 g (0.0219 mol) of the above base are dissolved in ether and a few drops of acetone, and a solution of hydrogen chloride in ether is then poured slowly therein until the pH is acid. A fine white solid appears; the mixture is stirred for 2 hours and the solid is then filtered off and washed with ether.

This solid is placed in contact for half an hour with refluxing methyl ethyl ketone containing a few drops of isopropanol, the mixture is then left to cool and the solid is filtered off, washed carefully and dried in vacuo at 80° C. It is a finely crystalline white compound. Melting point = 171.5°–172.5° C. (decomposition).

The propionamidoxime derivatives were subjected to various biological tests which demonstrated their activity in the field of the central nervous system.

The acute toxicity was determined on mice after intraperitoneal injection.

It is of the order of 50 to 200 mg/kg.

The therapeutic acitivity of the propionamidoxime derivatives was determined in several fields.

1. The action on the central nervous system was determined using the "Eating test" (described by R. J. Stevens, Brit. J. Pharmacol., 49, 146 (1973)).

In this test, the propionamidoxime derivatives favour the intake of food by the animals, this behaviour reflecting an anxiolytic action.

2. The antidepressive action was determined by the test for the antagonism towards ptosis caused by reserpine (C. Gouret et al., J. Pharmacol. (Paris), 8, 333–350 (1977)).

The mice (male, CD1 Charles River, France, weighing 18-22 g) simultaneously received the products to be studied or the solvent (administered intraperitoneally) and reserpine (4 mg/kg, administered subcutaneously).

After sixty minutes, the degree of palpebral ptosis is estimated for each mouse by means of a rating scale (0 to 4).

For each dose, the mean rating and the percentage variation relative to the control batch are calculated.

For each product, the AD 50, namely the dose which reduces the mean ptosis score by 50%, relative to the controls, is determined graphically.

The AD 50 varies from 2 to 10 mg/kg, administered intraperitoneally.

These data show that the propionamidoxime derivatives can be used for the treatment of various affections, in particular for the treatment of various affections of the central nervous system and for the treatment of depression.

The propionamidoxime derivatives can be formulated as a pharmaceutical composition containing a said derivative and a pharmaceutically acceptable excipient. The composition can be in any form which is suitable for oral, parenteral or endorectal administration, for example in the form of tablets, dragees, sugar-coated pills, solutions to be taken orally or injected.

The daily posology can range from 5 to 500 mg.

We claim:

1. A compound of the formula:

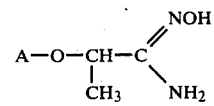

wherein A is tetrahydronaphthyl or dihydronaphthyl, or a pharmaceutically acceptable salt thereof.

2. A compound of claim 1, wherein A is 5,6,7,8-tetrahydronaphthyl-1- yl.

3. A compound of claim 1, wherein A is 5,8-dihydronaphthyl--yl.

4. A compound of claim 1, wherein A is 7,8-dihydronaphthyl-1-yl.

5. A pharmaceutical composition suitable for the treatment of depression which comprises an effective amount a compound of claim 1, 2 3 or 4 and a pharmaceutically acceptable excipient.

6. A method of treating a patient to retard depression which comprises administering to said patient an effective amount of a compound of claim 1, 2, 3 or 4 capable of retarding depression in said patient.

* * * * *

UNITED STATES PATENT AND TRADEMARK OFFICE
CERTIFICATE OF CORRECTION

PATENT NO. : 4,265,911
DATED : May 5, 1981
INVENTOR(S) : Henry NAJER ET AL

It is certified that error appears in the above—identified patent and that said Letters Patent is hereby corrected as shown below:

Column 3, line 7: change "$M_gSO_4$" to --$MgSO_4$--

Signed and Sealed this

Ninth Day of February 1982

[SEAL]

Attest:

GERALD J. MOSSINGHOFF

Attesting Officer    Commissioner of Patents and Trademarks